United States Patent [19]

Fujieda

[11] Patent Number: 5,420,652

[45] Date of Patent: May 30, 1995

[54] VISUAL ACUITY TEST MARK DISPLAYING DEVICE

[75] Inventor: Masanao Fujieda, Toyohashi, Japan

[73] Assignee: Nidek Co., Ltd., Japan

[21] Appl. No.: 903,290

[22] Filed: Jun. 24, 1992

[30] Foreign Application Priority Data

Jun. 29, 1991 [JP] Japan .................... 3-185449

[51] Int. Cl.⁶ .............................................. A61B 3/02
[52] U.S. Cl. ........................ 351/239; 351/200; 369/24
[58] Field of Search ............... 351/239, 240, 241, 242, 351/243, 244, 200, 237; 369/24, 30; 364/525, 550, 551.01

[56] References Cited

U.S. PATENT DOCUMENTS

| | | | |
|---|---|---|---|
| 3,969,020 | 7/1976 | Lynn et al. | 351/237 |
| 4,740,072 | 4/1988 | Griffin et al. | 351/244 |
| 4,753,527 | 6/1988 | Ishihara | 351/244 |
| 4,861,156 | 8/1989 | Terry | 351/243 |
| 4,869,589 | 9/1989 | Blair et al. | 351/244 |
| 5,121,981 | 6/1992 | Waltuck et al. | 351/243 |
| 5,129,720 | 7/1992 | Jovicevic | 351/243 |
| 5,206,671 | 4/1993 | Eydelman et al. | 351/203 |

FOREIGN PATENT DOCUMENTS

| | | | |
|---|---|---|---|
| 63147429 | 6/1968 | Japan . | |
| 3147429 | 6/1986 | Japan | A61B 3/02 |

*Primary Examiner*—Loha Ben
*Assistant Examiner*—Darryl J. Collins
*Attorney, Agent, or Firm*—Finnegan, Henderson, Farabow, Garrett & Dunner

[57] ABSTRACT

A visual acuity test mark displaying device comprises: a test mark selecting means provided with a plurality of test mark selecting keys which are operated for the sequential selection of visual acuity test marks; a display means for displaying visual acuity test marks selected by the test mark selecting means at a predetermined position; a specifying means for specifying optional key-mark combinations each of a test mark selecting key and a visual acuity test mark selected by operating the same test mark selecting key; an input means for entering data representing the arrangement of the visual acuity test marks specified by the specifying means; and a storage means for storing the optional key-mark combinations specified by the specifying means. The visual acuity test mark displaying device can be set for visual acuity test mark sets desired by the user and enables the change of the visual acuity test mark sets for which the same is set beforehand.

6 Claims, 9 Drawing Sheets

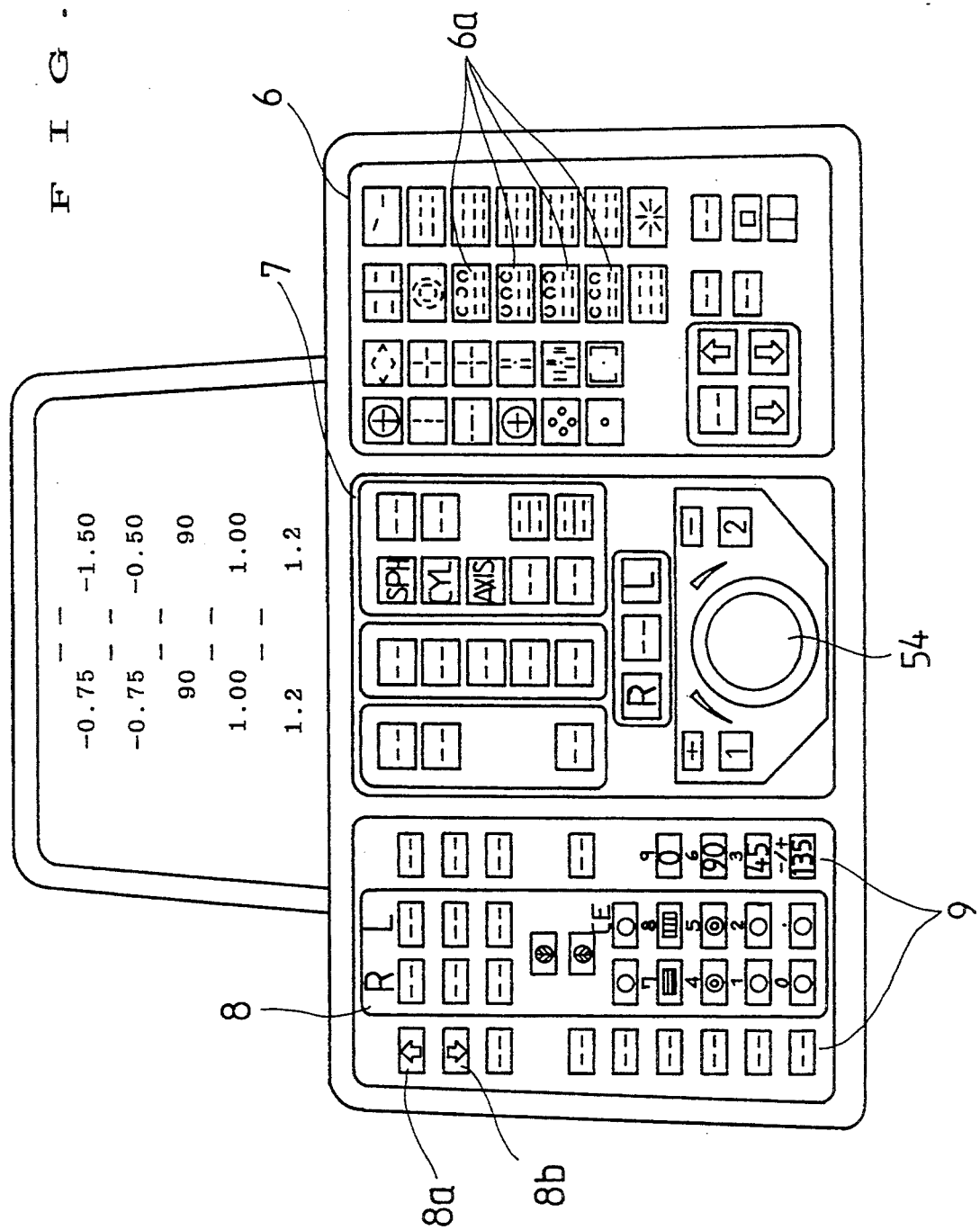

FIG. 5

| Type of vision test chart | | Code | Visual acuity/Code | | | | Auxiliary lens | Controlled variables of electronic dial |
|---|---|---|---|---|---|---|---|---|
| | | | Visual acuity | Code | Visual acuity | Code | | |
| Landolt | | K1 | 0.05 | V1 | 0.63 | V14 | | SPH |
| SNELLEN | | K2 | 0.063 | V2 | 0.7 | V15 | | |
| Alphabet | | K3 | 0.08 | V3 | 0.8 | V16 | | |
| Numeral | | K4 | 0.1 | V4 | 0.9 | V17 | | |
| Hiragana | | K5 | 0.125 | V5 | 1.0 | V18 | | |
| Pattern(Infant) | | K6 | 0.16 | V6 | 1.2 | V19 | | |
| Pattern(Preliminary) | | K7 | 0.2 | V7 | 1.25 | V20 | | |
| | | | 0.25 | V8 | 1.4 | V21 | | |
| | | | 0.3 | V9 | 1.5 | V22 | | |
| | | | 0.32 | V10 | 1.6 | V23 | | |
| | | | 0.4 | V11 | 2.0 | V24 | | |
| | | | 0.5 | V12 | | | | |
| | | | 0.16 | V13 | | | | |
| Degree of astigmatism (Dense) | □ | K8 | | | | | | CYL or AXIS |
| Degree of astigmatism (Coarse) | ⋮ | K9 | | | | | | |
| R/G | | K10 | | | | | | SPH |
| C C | | K11 | | | | | | CYL or AXIS |
| Pattern(Preliminary) | [·] | K12 | | | | | ◍ Red filter / ◍ Polarizing filter | SPH |
| | [·] | K13 | | | | | ◍ / ◍ | |
| Polarization R/G | ▦ | K14 | | | | | ◍ / ◍ | PRISM |
| | | K15 | | | | | ◍ / ◍ | |
| Obliquity | ⊢ | K16 | | | | | ◍ / ◍ | SPH |
| Obliquity | ⊢ | K17 | | | | | ◍ / ◍ | PRISM |
| | | K18 | | | | | ◍ / ◍ | PRISM |
| Obliquity | ⊕ | K19 | | | | | Ⓡ Red filter / Ⓖ Green filter | PRISM |

OPEN/OCCLUDER selected by selecting the eye to be examined, R/L/B

OYL or AXIS

VISUAL ACUITY TEST MARK DISPLAYING DEVICE

BACKGROUND OF THE INVENTION

1. Field of the Invention

The present invention relates to a visual acuity test mark displaying device (hereinafter referred to as "test mark displaying device") provided with a visual acuity test mark selecting means for selecting a desired visual acuity test mark (hereinafter referred to as "test mark") among a plurality of test marks.

2. Description of the Related Art

Recently, computer technology has been incorporated into vision testers, and vision testers provided with a microcomputer are prevalent in recent years. Computer-aided control techniques are applied to the control of test marks of vision test chart projectors and vision testers, such as backlighted vision test charts of a polar chart type and a panel type. These vision testers are provided with a remote controller for changing the test marks, operated by the tester in changing the test marks. A known vision tester cooperates with another apparatus, such as an refractor, i.e., what is called a motor-driven phoroptor, for efficient vision testing.

Incidentally, although Landolt rings are most prevalent test marks of the vision test chart, characters and marks other than Landolt rings are used in addition to Landolt rings. The combination and arrangement of these test characters and test marks are specified in national standards or determined by national or local convention. The vision tester is required to be capable of ophthalmic tests including an astigmatic vision test, a cross-cylinder test muscle barance test and a stereoscopic vision test etc., and these tests employ different test mark sets, respectively.

Accordingly, the vision tester manufacturers need to manufacture vision testers provided respectively with different types of vision test charts, and the test mark control program must be modified so as to meet the control of the vision test chart employed in the vision testers.

A procedure of modifying the visual test mark control program will be described in connection with a control circuit included in a conventional vision tester.

FIG. 1 shows the appearance of a remote controller for controlling a vision test chart projector. The arrangement of switches on the remote controller and test marks are dependent on user's option. FIG. 2 shows the circuit of the remote controller. When the chart selector switch 61 is depressed, a predetermined code digital signal is occurred by microcomputer 62, the signal is converted into a code optical pulse signal by a light emitting element 68 through code modulation circuit 64 and output buffer 66, and is transferred to the vision test chart projector. Generally, the switching circuit of the remote controller is a switching matrix because the remote controller deals with a plurality of test marks.

The following modifications are made in manufacturing a vision test chart projector to project a specified vision test chart.

1. A glass chart disk carrying various vision test charts formed thereon by photographic printing processes is fabricated.

2. Indications on the operating panel of the remote controller are changed.

3. The chart disk is driven by a motor and a table tabulating code signals representing individual test marks, and the corresponding number of pulses representing steps of operation of the motor is rewritten to make the operation of the selector keys provided on the operating panel of the remote controller coincide with that of the chart disk and, if necessary, a mask disk and the program is modified.

A vision tester which cooperates with a refractor, such as disclosed in Japanese Patent Application Laid-Open No. Sho 63(1988)-147429, controls both the vision tester and the refractor by means of the test mark selector key of the remote controller. A wireless remote controller employs a special IC chip capable of operating at a low power consumption so that the wireless remote controller can be driven by a battery. Therefore, the code signals determined by the switching matrix circuit of this vision tester, in most cases, do not coincide with those determined by the switching matrix circuit of the refractor. Accordingly, the code signals corresponding to the test mark selector switch of the controller of the refractor are converted into those provided by the wireless remote controller for controlling the vision tester. In this refractor, the following modifications are made, in addition to the modification of the program for controlling the refractor, to deal with the change of the test mark set.

1. Indications on the operating panel are changed.

2. The code signals provided by operating the operating panel are changed for the code signals for controlling the vision tester, and the program is modified.

3. A table tabulating the objects of operation of an electronic dial provided on the operating panel, and data for selecting the right and left auxiliary lenses is rewritten and the program is modified.

Problems requiring the inefficient manufacture of many types of vision testers cannot be solved unless an international standard test mark set is established. The modification of the program according to the change of the test mark set requires very complicated work. A vision tester that cooperates with another refractor, in particular, requires the modification of an extensive portion of the program including a portion specific to the control of the vision tester, which is a primary cause of increase in the manufacturing cost of the apparatus.

SUMMARY OF THE INVENTION

The present invention has been made to solve the foregoing problems in the prior art, and it is therefore an object of the present invention to provide a visual acuity test mark displaying device capable of readily dealing with control operation required by any test mark set.

Another object of the present invention is to provide a vision tester provided with a test mark displaying device capable of readily dealing with control operation required by any test mark set.

To achieve the objects, the present invention provides a visual acuity test mark displaying device comprising:

a test mark selecting means provided with a plurality of test mark selecting keys which are operated for the sequential selection of test marks to be displayed;

a display means for displaying a visual acuity test mark selected by the test mark selecting means at a predetermined position;

a specifying means for specifying optional key-mark combinations of each test mark selecting key and a test mark selected by operating the same test mark selecting key;

an input means for entering the position of the specified selected test mark; and a storage means for storing the optional key-mark combinations specified by the key-mark combination specifying means.

The test mark selecting means is provided with a mode selector switch for selecting either a specifying mode or an input mode, and the test mark selecting means is used in combination with the specifying means and the input means.

The specifying means and the input means are included in an operator's console which can be connected to the visual acuity test mark displaying device.

The visual acuity test mark displaying device is provided with a display means for the confirmation of rewritten information.

The information stored in the storage means includes position data representing position on the test mark selecting means, data representing the types of test marks and data representing the disposition of test marks.

The storage means is detachably connected to an IC connector and has a ROM storing a program for transferring the information stored in the storage means to a nonvolatile memory and for writing the information stored in the nonvolatile memory in the storage means connected to the IC connector.

The visual acuity test mark displaying device has a means for disposing an optical device corresponding to a signal provided by the test mark selecting means in the test window of an refractor unit.

The visual acuity test mark displaying device of the present invention requires the least necessary modifications in dealing with combinations of various visual acuity testing marks.

A test mark set established for the visual acuity test mark displaying device can readily be changed without requiring much time when necessary.

BRIEF DESCRIPTION OF THE DRAWINGS

The above and other objects, features and advantages of the present invention will become more apparent from the following description taken in connection with the accompanying drawings, in which:

FIG. 4 is a plan view of an operator's console included in the visual acuity test mark displaying device of FIG. 3;

FIG. 5 is an illustration of assistance in explaining a test mark code table stored in a ROM;

DESCRIPTION OF THE PREFERRED EMBODIMENTS

A visual acuity test mark displaying device in a preferred embodiment according to the present invention will be described hereinafter with reference to the accompanying drawings.

Figure 1:
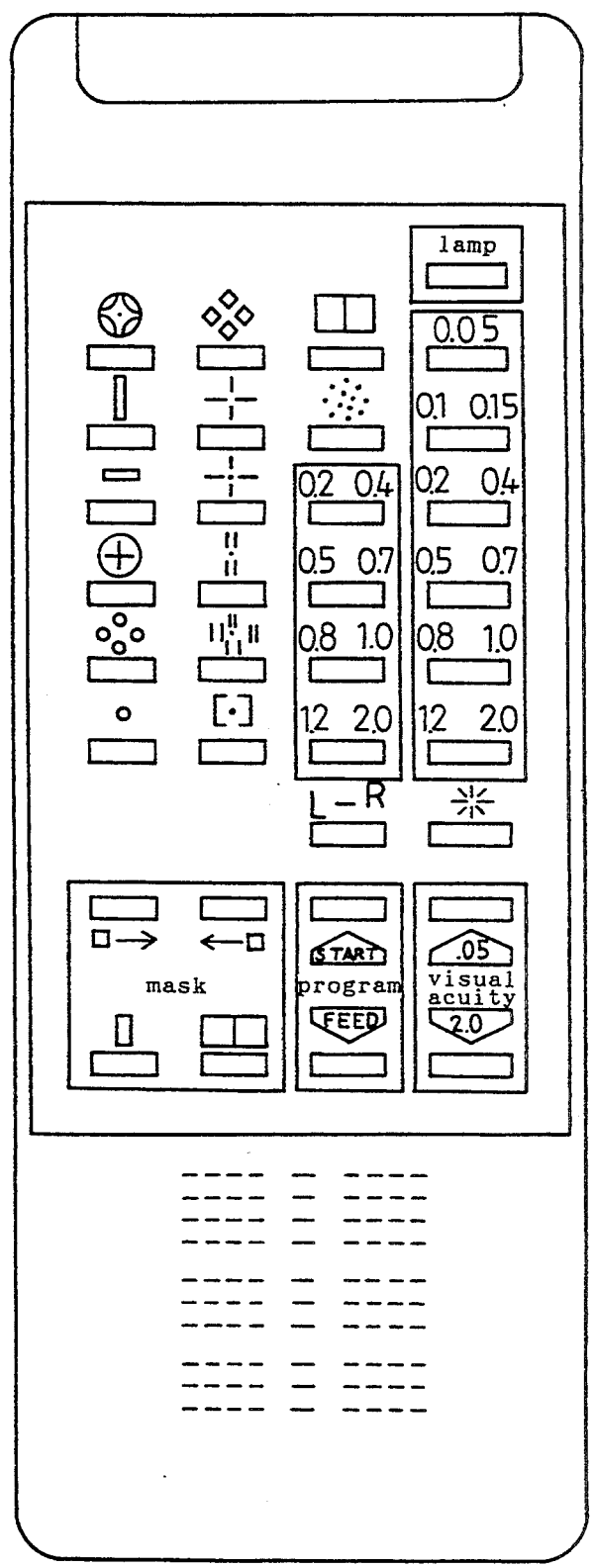
FIG. 1 is a plan view of a remote controller for controlling a prior art vision test chart projector.
Figure 2:
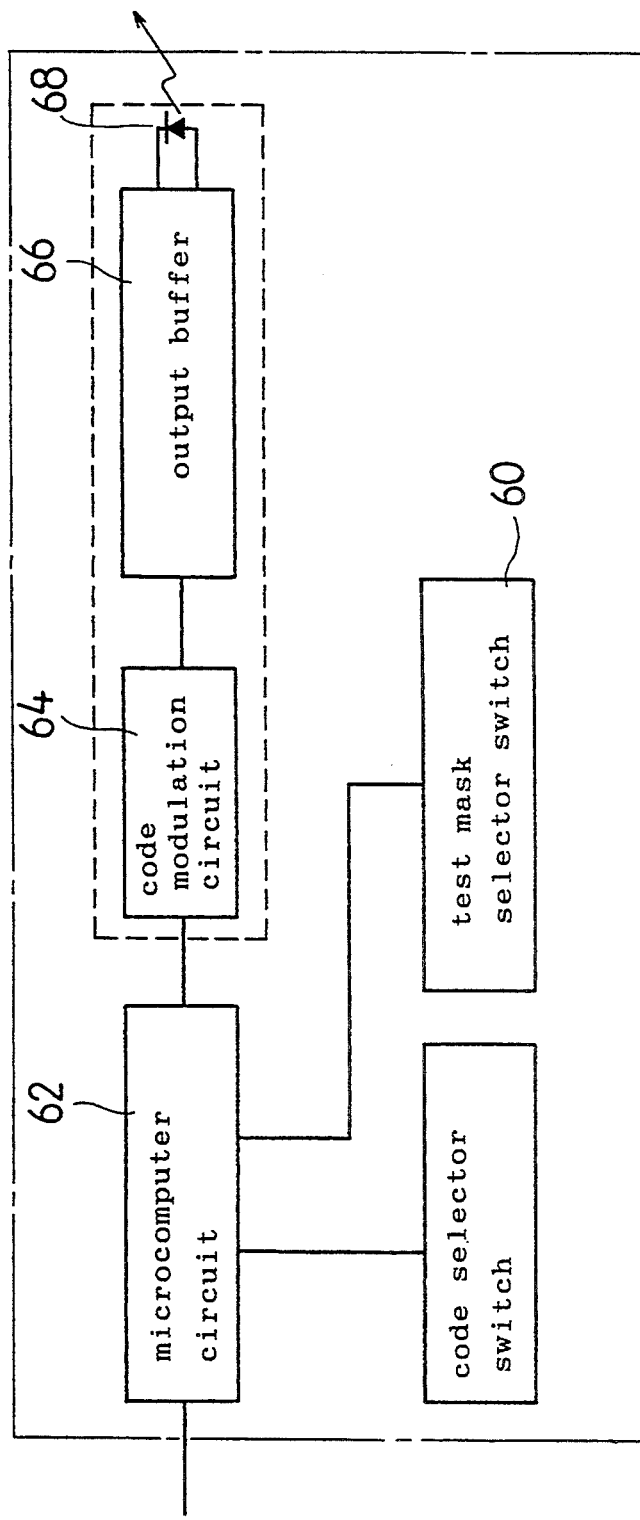
FIG. 2 is a block diagram showing the circuit configuration of the remote controller of FIG. 1.
Figure 3:
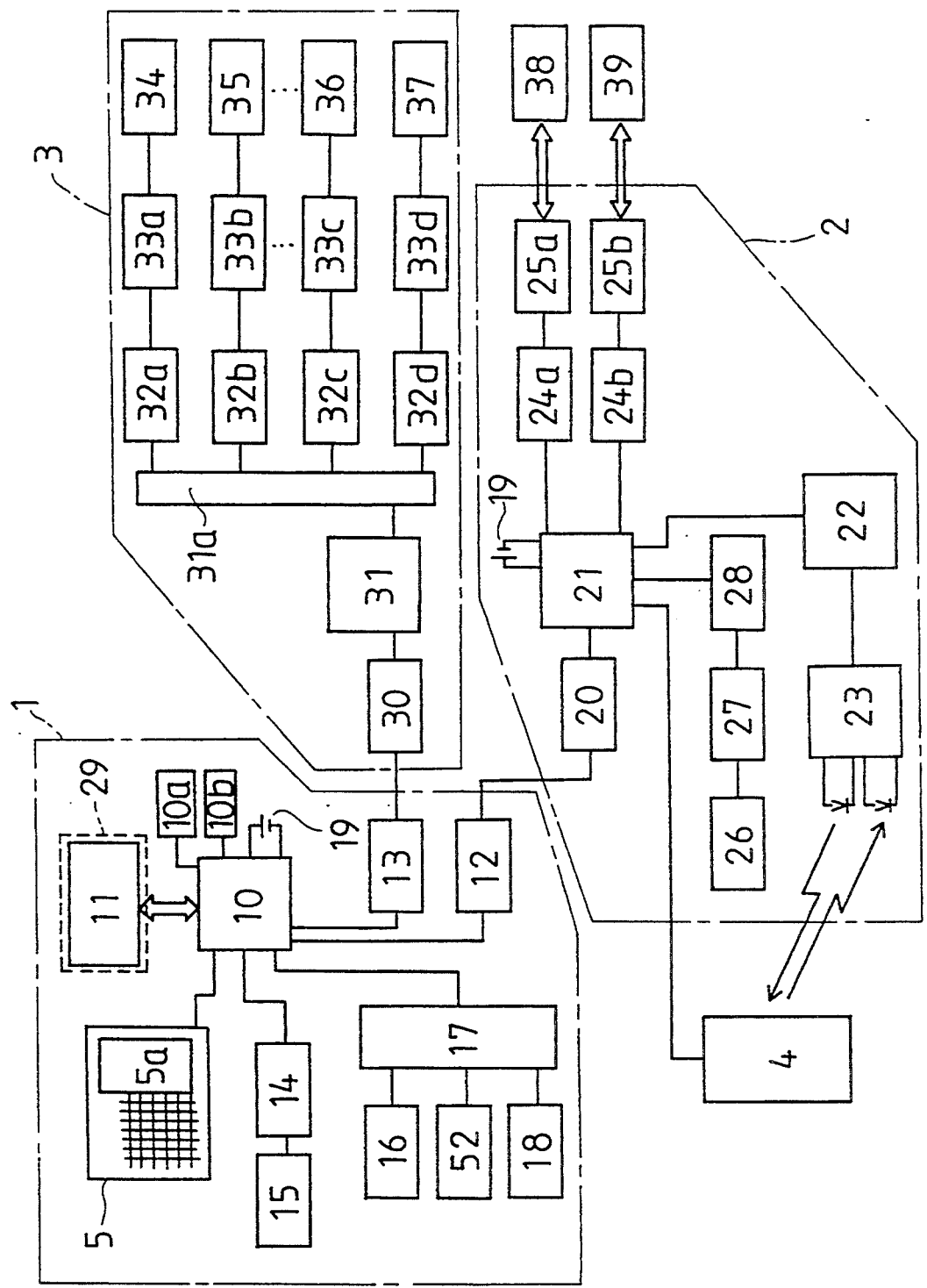
FIG. 3 is a block diagram of a visual acuity test mark displaying device in accordance with the present invention combined with a vision test chart projector and a refractor.

Referring to FIG. 3, a visual acuity test mark displaying device comprises an operating unit 1, a relay unit 2, an refractor 3 and a vision test chart projector 4.

(Operating Unit 1)

A matrix switching circuit 5 is connected through a key encoder 5a to a microcomputer 10. The elements of the matrix switching circuit 5 and the keys of an operator's console OP are in one-to-one correspondence. The arrangement of the keys of the operator's console OP is shown in FIG. 4. Provided on the operator's console OP are test mark selector keys 6 each for selecting a test mark set and for setting an auxiliary lens necessary for using the selected test mark set in the test window of the refractor 3, mode selector keys 7 each for selecting an operating mode of the refractor 3, auxiliary lens selector keys 8 each for selecting an auxiliary lens, and other function selector keys 9. These keys are used also for changing the test mark set. The operator's console OP is provided with an electronic dial 54 for the centralized operation of switches combined with those keys. Test mark sets, visual acuities and data representing the disposition of test marks are stored in a nonvolatile memory 11 connected to the microcomputer 10.

A matrix signal provided by operating the test mark selector key is given to the microcomputer 10. Then, the matrix signal is converted into signals representing the type of the test marks, visual acuities and the arrangement of the test marks on the disk of the vision test chart projector 4 on the basis of the data stored in the nonvolatile memory 11. Codes representing types of test marks, types of the auxiliary lenses, tables of visual acuities and a program for controlling operation for rewriting the contents of the nonvolatile memory 11 are stored in a ROM 10a. Data representing the arrangement of test marks are contained in a table (FIG. 5) stored in a nonvolatile memory provided in the test mark projector 4.

The nonvolatile memory 11 is connected detachably to an IC connector 29. All the contents of the nonvolatile memory 11 can be written in another nonvolatile memory 11 connected to the IC connector 29 by transferring all the contents of the nonvolatile memory 11 to a RAM 10b according to the program stored in the ROM 10a and writing the contents of the RAM 10b in the nonvolatile memory 11 connected to the IC connector 29. A LED display 15 is connected through a display driver 14 to the microcomputer 10. The matrix signal applied to the microcomputer 10 is converted into a code signal representing a type of test marks, the code signal is transferred through the display driver 14 to the LED display 15 to display the operated key 6 among the test mark selector keys 8 and test items on the LED display 15.

A rotary encoder 16 connected to electronic dial, a response switch 52 to be operated by the tester, and a dip switch 18 are connected through an I/O circuit 17 to the microcomputer 10. The rotary encoder 16 gives a signal to change SPH, CYL or Axis value the refractor of the refractor 3 through the I/O circuit 17 to the microcomputer 10. The key of the dip switch 18 for setting a code rewriting mode is provided on the back surface of the operating unit 1.

(Relay Unit 2)

An infrared remote controller 23 is connected through an I/O circuit 22 to a microcomputer 21 included in the relay unit 2. The microcomputer 10 of the operating unit 1 and the microcomputer 21 of the relay unit 2 are interconnected by RS-232C interfaces 12 and 20. The code signal rewritten by the microcomputer 10 are transferred through the interfaces 12 and 20 to the microcomputer 21. The microcomputer 21 gives the code signal and a signal representing position on the disk through the I/O circuit 22 to the infrared remote controller 23, and the infrared remote controller 23 converts the input signals into infrared signals and sends the infrared signals to the vision test chart projector 4.

The relay unit 2 and the vision test chart projector 4 in this embodiment are interconnected by an infrared bidirectional optical communication system, which may employ infrared signals or signal lines for connecting the relay unit 2 and the vision test chart projector 4.

An automatic ocular refractometer 38 and a lens meter 39 can be connected through RS-282C interfaces 24a and 24b and communication ports 25a and 25b to the microcomputer 21. Data measured by the automatic ocular refractometer 38 and the lens meter 39 are transferred through the microcomputers 21 and 10 to the refractor 3 to set the refractor 3 for initial values. The microcomputer 21 is connected through an I/O circuit 28 and a printer control circuit 27 to a printer 26. Measured data obtained by the refractor 3, the automatic ocular refractometer 38 and the lens meter 39 are transmitted through the I/O circuit 28 and the printer control circuit 27 to the printer 16 to print the measured data.

(Refractor 3)

Pulse motor drivers 32a, 32b, 32c and 32d for driving motors 33a, 33b, 33c and 33d respectively for driving a weak spherical lens disk 34, a strong spherical lens disk 35, an auxiliary lens disk 36 and a cross cylinder disk 37 are connected through an I/O circuit 31a to a microcomputer 31. Code signals provided by operating the mode selector keys 7, the auxiliary lens selector keys 8 and the function selector keys 9 are transmitted through RS-232C interfaces 13 and 30 to the microcomputer 31. The microcomputer 31 drives the pulse motor drivers 32a to 32d according to the input signals, and then, the pulse motor drivers 32a to 32d drives the weak spherical lens disk 34, the strong spherical lens disk 35 and the auxiliary lens disk 36 the cross cylynder disk 37 by the motors 33a to 33d, respectively, to place an optical device having optical characteristics specified by operating the keys of the operating unit 1 and the rotary encoder 16 in the vision test window of the refractor 3.

The microcomputer 10 specifies the type and position of the auxiliary lens required for the vision test on the basis of the code signals provided by operating the test mark selector keys 6, and signals representing the type and position of the auxiliary lens are given to the refractor 3. The microcomputer 31 controls the pulse motor driver 32c to drive the motor 33c so as to position the auxiliary lens disk 36 properly.

(Vision Test Chart Projector 4)

Figure 6:
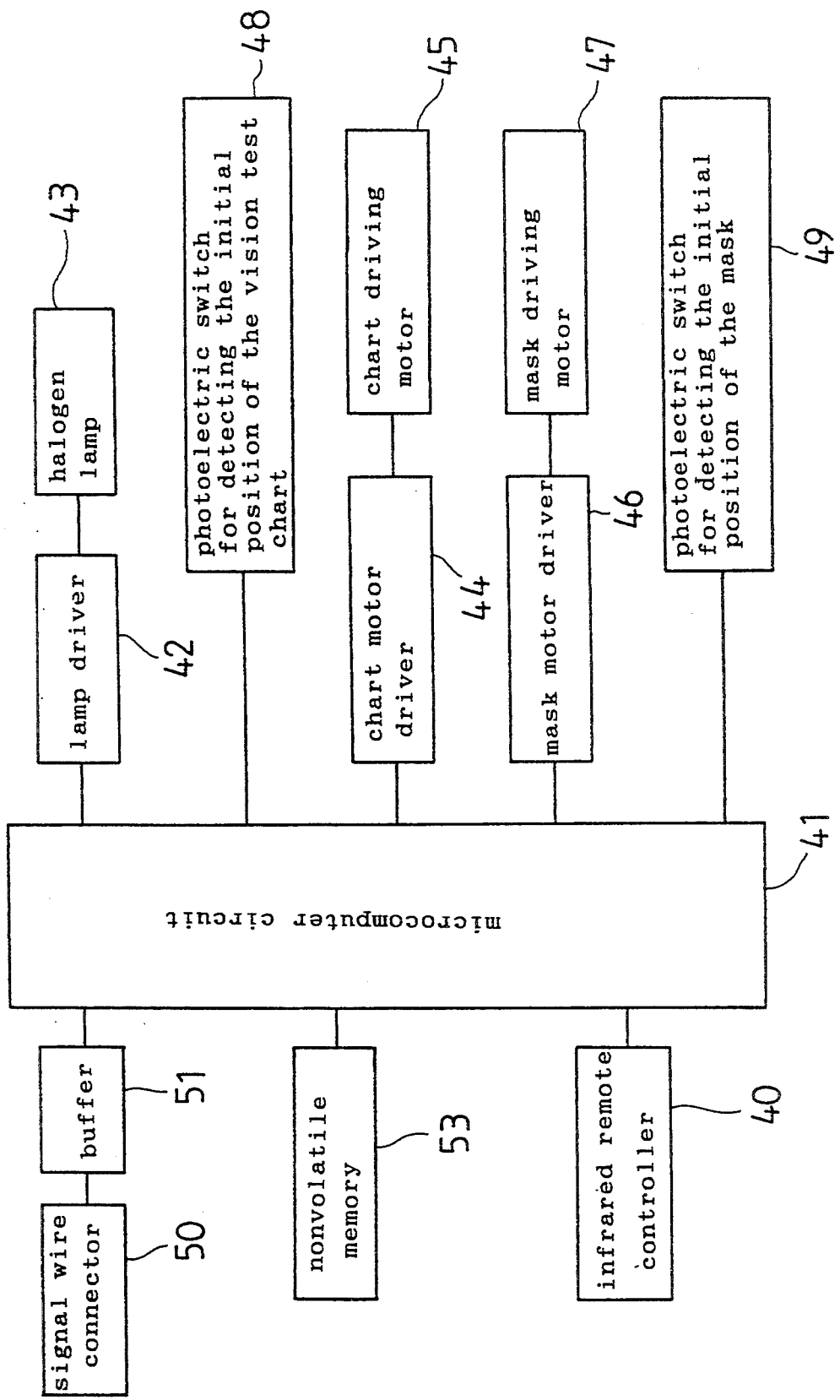
FIG. 6 is a block diagram of a controller for controlling the vision test chart projector of FIG. 3.

FIG. 6 is a block diagram of assistance in explaining the operation of the vision test chart projector 4.

An infrared remote controller 40, which exchanges signals with the infrared remote controller 23 of the relay unit 2, is connected to a microcomputer 41. Infrared signals provided by the relay unit 2 and received by the infrared remote controller 40 are applied to the microcomputer 41 after the same have been amplified and modulated. A test mark disk and, if necessary, a mask disk are operated on the basis of code signals representing the type of test marks, visual acuity values and the arrangement of the test marks. A table containing data representing the arrangement of the test marks may be stored in a nonvolatile memory included in the vision test chart projector 4. Upon the completion of the operation of the vision test chart projector 4 according to the signals provided by the relay unit 2, the microcomputer 41 provides an operation completion signal. The operation completion signal is sent to the infrared remote controller 23 of the relay unit 2 after modification by the infrared remote controller 40. The operation completion signal may be transmitted by a signal line.

A halogen lamp 43, i.e., a light source, is connected through a lamp driver 42 to the microcomputer 41. The operation of the halogen lamp 43 is controlled by the microcomputer 41. A chart driving motor 45 for rotating a test mark disk is connected through a motor driver 44 to the microcomputer 41. A mask driving motor 47 for rotating a mask disk for masking the test mark is connected through a motor driver 46 to the microcomputer 41. To the microcomputer 41 are also connected a photoelectric switch 48 for detecting the initial position of the test mark disk and a photoelectric switch 49 for detecting the initial position of the mask disk. The motors are controlled on the basis of detection signals provided by the photoelectric switches 48 and 49. The microcomputer 21 of the relay unit 2 and the microcomputer 41 of the vision test chart projector 4 are interconnected through a signal wire connector 50 and a buffer 51. The microcomputers 10 and 21 are backed up by back-up batteries 19, 19 respectively.

Figure 7:
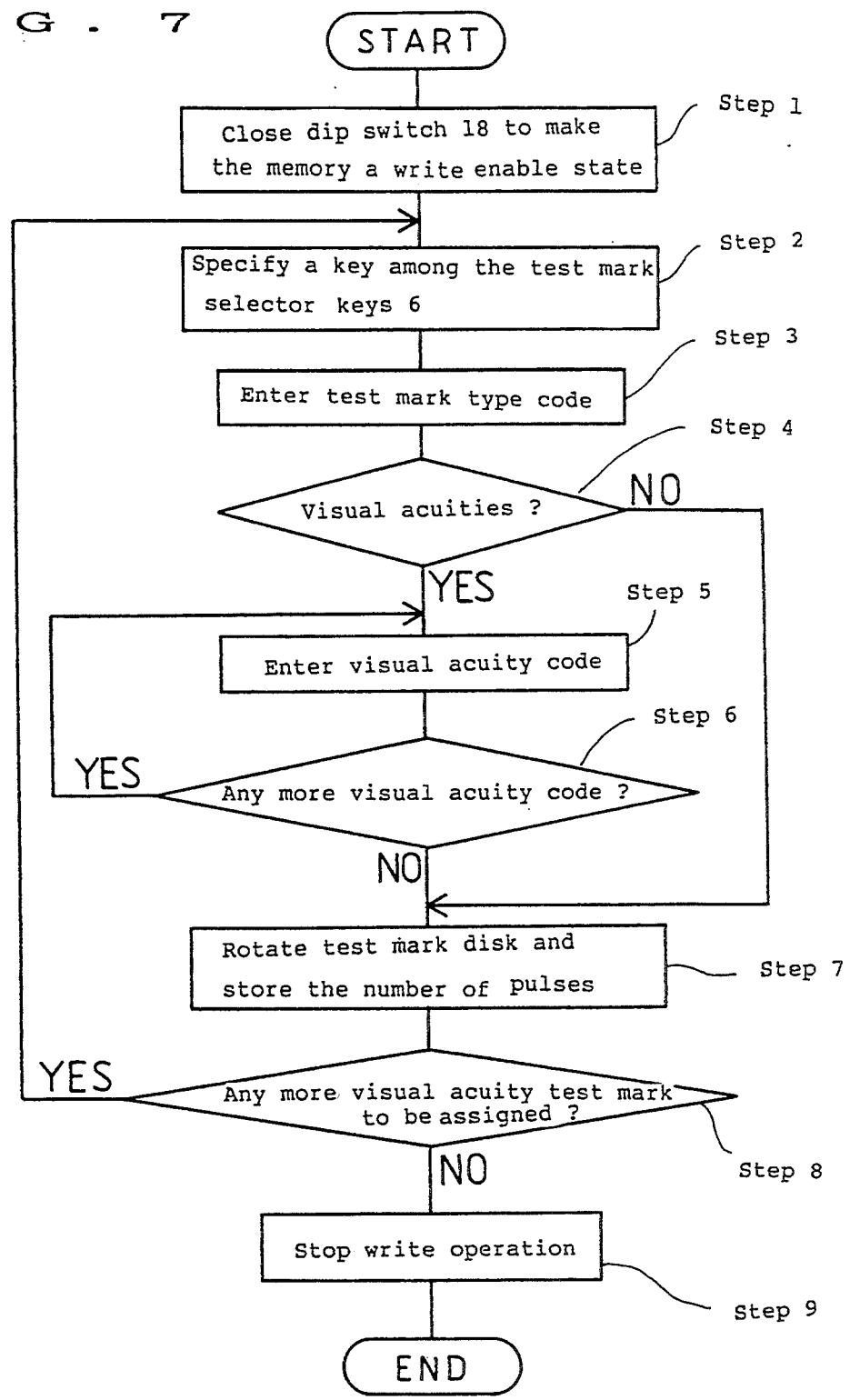
FIG. 7 is a flow chart of a procedure of modifying a program to deal with the change of the visual acuity test mark set.
Figure 8:
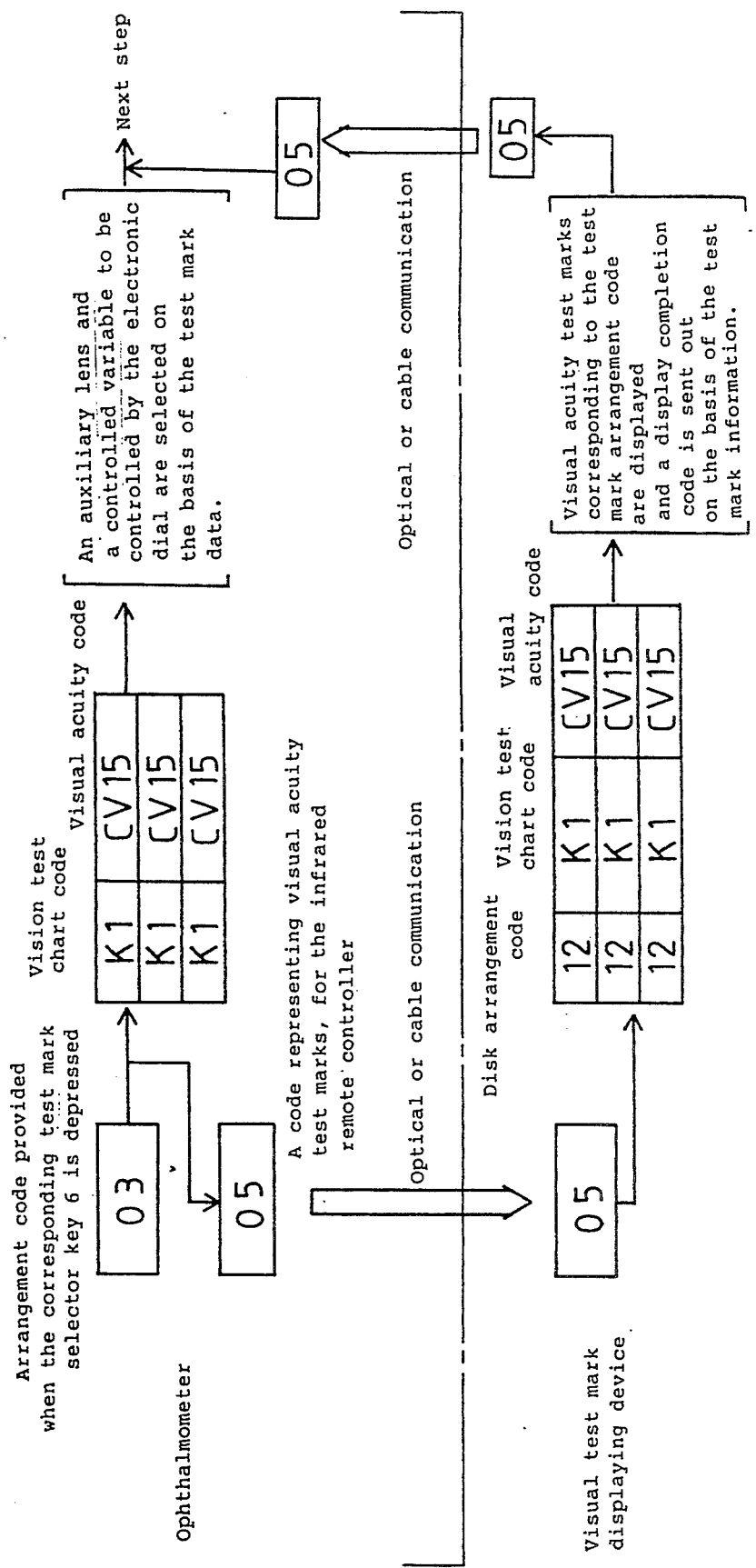
FIG. 8 is an illustration of assistance in explaining a method of using test mark codes in testing visual acuity.

A program changing procedure to be executed by the visual acuity test mark displaying device having the foregoing configuration to deal with the change of the test mark set will be described hereinafter with reference to FIG. 7.

In step 1, the key of the dip switch 18 provided on the back surface of the case of the operating unit 1 is operated to set the nonvolatile memory 11 in a write enable state. A key among the test mark selector keys 6 to which a test mark set is to be assigned is specified in step 2. A decimal test mark type code identifying the test mark set among those displayed on the LED display 15 of the operating unit 1 is entered in step 3 by operating the auxiliary lens selector keys serving also as numeric keys. Visual acuity codes are entered for visual acuity test marks. All the visual acuity codes of visual acuities displayed in one frame are entered sequentially in steps 4, 5 and 6. The vision test chart driving motor 45 is controlled through the communication line by operating an up key 8a and a down key 8b among the function selector keys 9 to turn the test mark disk of the vision test chart projector 4 in either a clockwise direction or a counterclockwise direction so that the test mark is positioned in place. The number of pulses corresponding to the distance between a reference position and the position of the test mark is calculated on the basis of the output signal of the photoelectric switch 48 for detecting the initial position and the number of driving pulses applied to the motor 45. In step 7, a specified key is depressed to store the number of pulses representing the distance between the reference position and the position of the test mark. The respective positions of the test marks on the disk may be determined beforehand and codes may be assigned respectively to the test, marks to enable the position of the test mark on the disk to be specified by entering the code by operating the numeric keys. Thus, instructions to be given to the test mark projector 4, the refractor 3 and, if necessary, the display are assigned to the keys, and the instructions can be written in the nonvolatile memory 11.

The foregoing steps are repeated to assign the test marks to the test mark selector keys 6 (steps 8 and 9). Thus, the visual acuity test mark displaying device is able to use a desired test mark set.

The operation of the visual acuity test mark displaying device thus programmed for testing visual acuity by using the new test mark set of, for example, Landolt rings for visual acuities 0.7, 0.8 and 0.9 will be described hereinafter.

Let's suppose that the switching circuit 5 provides a code signal representing an arrangement code "03" when the key 6a for selecting the Landolt test chart is depressed. A code signal representing the code "03" is given to the microcomputer 10. This code represents Landolt rings for visual acuities 0.7, 0.8 and 0.9. A vision test chart type code "K1" and visual acuity codes "V15", "V16" and "V17" representing the Landolt rings for visual acuities 0.7, 0.8 and 0.9 are stored in the nonvolatile memory 11. All the test marks correspond to the code "05" of the infrared remote controller for controlling the visual acuity test mark displaying device. The code "03" is converted into the code "05", the type of test is displayed on the display of the operator's console, and the code "05" is transmitted through the RS-232C interface 12 to the relay unit 2. The microcomputer 21 gives the code signal to the infrared remote controller 23, the infrared remote controller 23 converts the code signal into a corresponding infrared signal and gives the infrared signal to the test mark projector 4.

The vision test chart projector 4 demodulates the infrared signal and gives the demodulated signal to the microcomputer 41. A layout code "12" representing the position of the Landolt rings for visual acuities 0.7, 0.8 and 0.9 relative to a reference position on the test mark disk and corresponding to the code "05", the vision test chart code "K1" and visual acuity codes "V15", "V16" and "V17" are stored in a nonvolatile memory 53 connected to the microcomputer 41. The microcomputer 41 fetches the layout code "12" and drives the test mark disk to dispose a desired vision test chart at a displaying position.

Upon the completion of the operation of the vision test chart projector 4, the microcomputer 41 sends a code signal representing the code "05" through the communication line to the microcomputer 10. The microcomputer 10 sends data for driving a desired auxiliary lens disk on the basis of the vision test chart type code "K1" to the refractor 3 through the RS-232C interface 13, to make the pulse motor driver 32 drive the motor 33.

The controlled variable of the microcomputer 10 controlled by the electronic dial on the operator's console is a SPH term. A number of pulses of rotary encoder generated by turning of the electronic dial is transmitted through the RS-232C interface 13 to the pulse motor driver 32 to drive the spherical lens disk through a desired angle by the motor 33.

In specifying a test mark for the visual acuity 0.7 on the vision test chart, the arrow key on the operator's console is depressed. Then a code signal representing the arrow key is converted into a code representing a corresponding key on the wireless remote controller. The operating unit 1 sends a signal representing the key on the wireless remote controller to the relay unit 2, the relay unit 2 converts the input signal into a corresponding infrared signal, the vision test chart projector 4 converts the infrared signal into a mask disk position code, the mask driving motor 47 is driven according to the mask disk position code so that the Landolt rings for a visual acuity 0.7 is displayed and the Landolt rings for visual acuities of 0.8 and 0.9 are masked. After the mask disk has thus been positioned, the code "V15" is given as a mask disk positioning completion signal to the refractor 3. The visual acuity 0.7 is displayed at a predetermined position on the display of the operator's console of the refractor 3.

Although the visual acuity test mark displaying device has been described as combined with the refractor and the vision test chart projector, naturally, the visual acuity test mark displaying device may be used independently.

The present invention is applicable to an existing visual acuity test mark displaying device incapable of defining test mark set information, such as an infrared remote-controlled visual acuity test mark displaying device being presently used in an ophthalmic hospital, ophthalmic clinic or an optical shop. In applying the present invention to such an existing infrared remote-controlled visual acuity test mark displaying device, the refractor is provided with a function capable of storing codes sent out from the infrared remote controller of the visual acuity test mark displaying device, such as a remote controller with a learning function for operating a TV set or a VTR, to redefine the codes assigned to the remote controller for vision test chart type codes, visual acuity codes and the like in the refractor.

It is possible to use the automated functions of the refractor, such as a function for the automatic setting of auxiliary lenses, the selection of controlled variables (SPH, CYL, AXIS, PRISM and so forth) to be controlled by the electronic dial, and the storage of test mark displaying sequence (programs defining the vision testing procedure) on the basis of the test mark set information.

It is obvious from the foregoing description, the present invention is applicable to visual acuity test mark displaying devices of a panel chart type, a backlighted moving film type, a TV display type and an LCD display type.

Figure 9:
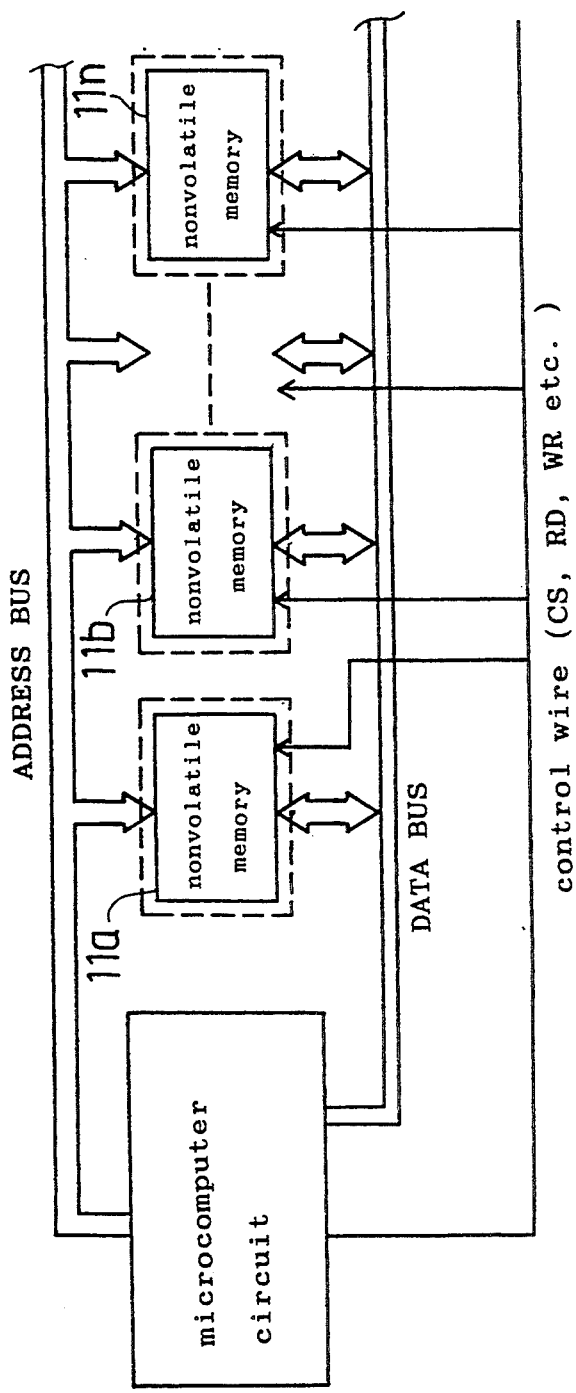
FIG. 9 is a block diagram of a circuit for writting a plurality of nonvolatile memories.

Furthermore, although the visual acuity test mark displaying device reads all the data stored in the nonvolatile memory, stores the same temporarily in the RAM and writes the data stored in the RAM in another nonvolatile memory. A special writing device as shown in FIG. 9 may create a large quantity of duplicates.

Any way, the present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A refractor cooperated with a test mark displaying device, comprising:

an operating unit comprising a matrix switching circuit having switching elements respectively corresponding to keys provided on an operator's console, first storage means storing data representing the types of visual acuity test marks, data representing visual acuities and data representing the arrangement of visual acuity test marks, second storage means storing code tables of the types of the visual acuity test marks stored in the first storage means and data representing visual acuities, and signal converting means for converting matrix signals provided by the matrix switching circuit into code signals representing the data stored in the first storage means on the basis of the data stored in the first storage means;

a relay unit comprising an infrared remote controller for modulating code signals provided by the signal converting means of the operating unit into infrared signals;

a refractor comprising a device arranging means for arranging a required optical device in a test window on the basis of a code signal provided by the signal converting means of the operating unit; and a vision test chart projector provided with a disk driving means for driving a vision test chart disk on the basis of an infrared code signal given thereto from the infrared remote controller of the relay unit;

wherein the operating unit is provided with a key assigning means for assigning keys respectively to visual acuity test marks, and a test mark input means for entering test mark codes representing visual acuity test marks, and the operating unit or the vision test chart projector is provided with a third storage means for storing test mark codes representing the visual acuity test mark codes positioned on a predetermined transmitting displaying surface by the test mark disk driving means, in correspondence with the keys assigned to the visual acuity test marks by the key assigning means, and wherein the third storage means is used in combination with the first storage means.

2. A refractor cooperated with a test mark displaying device, according to claim 1, wherein the first and third storage means are nonvolatile memories.

3. A visual acuity test mark displaying device, comprising:

an operating unit comprising a matrix switching circuit having switching elements respectively corresponding to keys provided on an operator's console, a first storage means storing data representing the types of visual acuity test marks, data representing visual acuities and data representing the arrangement of visual acuity test marks, a second storage means storing code tables of the types of the visual acuity test marks stored in the first storage means and data representing visual acuities, and a signal converting means for converting matrix signals provided by the matrix switching circuit into code signals representing the data stored in the first storage means on the basis of the data stored in the first storage means;

a visual acuity test mark display unit provided with a driving means for driving a visual acuity test mark arrangement means on the basis of a signal from the operating unit;

wherein the operating unit is provided with a key assigning means for assigning keys respectively to visual acuity test marks, and a test mark input means for entering test mark codes representing visual acuity test marks, and the operating unit or the vision test chart display unit is provided with a third storage means for storing test mark codes representing the visual acuity test mark codes positioned on the predetermined displaying surface by the vision test mark arrangement means, in correspondence with the keys assigned to the visual acuity test marks by the key assigning means.

4. A visual acuity test mark displaying device according to claim 3, wherein the visual acuity test mark display unit comprises a vision test chart projector provided with a disk driving means for driving a vision test chart disk.

5. A refractor cooperated with a visual acuity test mark displaying device, comprising:

an operating unit comprising a matrix switching circuit having switching elements respectively corresponding to keys provided on an operator's console, a first storage means storing data representing the types of visual acuity test marks, data representing visual acuities and data representing the arrangement of visual acuity test marks, a second storage means storing code tables of the types of the visual acuity test marks stored in the first storage means and data representing visual acuities, and a signal converting means for converting matrix signals provided by the matrix switching circuit into code signals representing the data stored in the first storage means on the basis of the data stored in the first storage means;

a refractor comprising a device arranging means for arranging a required optical device in a test window on the basis of a code signal provided by the signal converting means of the operating unit;

a vision test chart projector provided with a disk driving means for driving a vision test chart disk on the basis of an infrared code signal; and a relay unit for transmitting code signals provided by the signal converting means of the operating unit to the refractor and the vision test chart projector;

wherein the operating unit is provided with a key assigning means for assigning keys respectively to visual acuity test marks, and a test mark input means for entering test mark codes representing visual acuity test marks, and the operating unit or the vision test chart projector is provided with a third storage means for storing test mark codes representing the visual acuity test mark codes positioned on a predetermined transmitting displaying surface by the test mark disk driving means, in correspondence with the keys assigned to the visual acuity test marks by the key assigning means.

6. A refractor cooperated with a visual acuity test mark displaying device according to claim 5, wherein the relay unit comprises an infrared remote controller for modulating code signals provided by the signal converting means of the operating unit into the infrared signals.

* * * * *